United States Patent [19]

Schromm et al.

[11] 4,332,802
[45] Jun. 1, 1982

[54] 11-OXO-11H-PYRIDO[2,1-b]QUINAZOLINE-2-CARBOXYLIC ACID AND SALTS THEREOF, ANTIALLERGIC COMPOSITIONS CONTAINING IT AND METHODS OF SUPPRESSING ALLERGIC REACTIONS WITH IT

[75] Inventors: Kurt Schromm, Ingelheim am Rhein; Anton Mentrüp, Mainz-Kastel; Ernst-Otto Renth, Ingelheim am Rhein; Armin Fügner, Gau-Algesheim, all of Fed. Rep. of Germany

[73] Assignee: Boehringer Ingelheim KG, Ingelheim am Rhein, Fed. Rep. of Germany

[21] Appl. No.: 204,226

[22] Filed: Nov. 5, 1980

Related U.S. Application Data

[60] Continuation-in-part of Ser. No. 146,620, May 5, 1980, abandoned, which is a continuation of Ser. No. 64,010, Aug. 6, 1979, abandoned, which is a continuation of Ser. No. 953,753, Oct. 23, 1978, abandoned, which is a continuation of Ser. No. 853,034, Nov. 16, 1977, abandoned, which is a division of Ser. No. 750,725, Dec. 15, 1976, Pat. No. 4,083,980.

[30] Foreign Application Priority Data

Dec. 19, 1975 [DE] Fed. Rep. of Germany ....... 2557425

[51] Int. Cl.³ .................. A61K 31/505; C07D 487/04
[52] U.S. Cl. ...................................... 424/251; 544/252
[58] Field of Search ............... 544/250, 252, 246, 247; 424/251

[56] References Cited

U.S. PATENT DOCUMENTS

| | | | |
|---|---|---|---|
| 4,012,387 | 3/1977 | Schwender et al. | 544/246 |
| 4,033,961 | 7/1977 | Schwender et al. | 544/252 X |
| 4,066,767 | 1/1978 | Schwender et al. | 424/251 |
| 4,076,710 | 2/1978 | Schwender et al. | 424/251 X |
| 4,104,389 | 8/1978 | Schwender et al. | 424/251 |
| 4,142,049 | 2/1979 | Schwender et al. | 544/246 |
| 4,168,380 | 9/1979 | LeMahieu | 544/250 |
| 4,179,560 | 12/1979 | Yamamoto et al. | 544/250 |

FOREIGN PATENT DOCUMENTS

| | | | |
|---|---|---|---|
| 2739020 | 8/1977 | Fed. Rep. of Germany | 424/251 |
| 2812585 | 9/1978 | Fed. Rep. of Germany | |
| 2812586 | 9/1978 | Fed. Rep. of Germany | |
| 50-14699 | 2/1975 | Japan | 544/247 |
| 1242863 | 8/1971 | United Kingdom | 544/250 |

OTHER PUBLICATIONS

Khosla et al., Chemical Abstracts, vol. 49, 1059i (1955).
Sachdev et al., Chemical Abstracts, vol. 50, 12061h (1956).
Sharma et al., Chemical Abstracts, vol. 51, 8105h (1957).
Dhami et al., Chemical Abstracts, vol. 52, 5421d (1958).
Kaushal et al., Chemical Abstracts, vol. 71, 38898c (1969).

*Primary Examiner*—Mark L. Berch
*Assistant Examiner*—Diana G. Rivers
*Attorney, Agent, or Firm*—Hammond & Littell, Weissenberger & Muserlian

[57] ABSTRACT

This invention relates to the novel compound 11-oxo-11H-pyrido[2,1-b]quinazoline-2-carboxylic acid of the formula

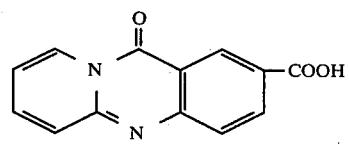

and non-toxic, pharmacologically acceptable salts thereof, as well as to pharmaceutical composition containing these compounds as active ingredients, and methods of using them as antiallergics.

3 Claims, No Drawings

11-OXO-11H-PYRIDO[2,1-b]QUINAZOLINE-2-CARBOXYLIC ACID AND SALTS THEREOF, ANTIALLERGIC COMPOSITIONS CONTAINING IT AND METHODS OF SUPPRESSING ALLERGIC REACTIONS WITH IT

This is a continuation-in-part of copending application Ser. No. 146,620, filed May 5, 1980, now abandoned; which in turn is a continuation of application Ser. No. 64,010, filed Aug. 6, 1979, now abandoned; which in turn is a continuation of application Ser. No. 953,753, filed Oct. 23, 1978, now abandoned; which in turn is a continuation of application Ser. No. 853,034, filed Nov. 16, 1977, now abandoned, which in turn is a division of application Ser. No. 750,725, filed Dec. 15, 1976, now U.S. Pat. No. 4,083,980, granted Apr. 11, 1978.

This invention relates to the novel compound 11-oxo-11H-pyrido[2,1-b]quinazoline-2-carboxylic acid of the formula

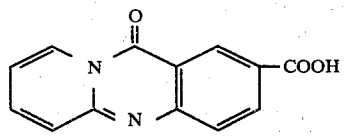

and non-toxic, pharmacologically acceptable salts thereof, as well as to pharmaceutical compositions containing these compounds as active ingredients, and methods of using them as antiallergics.

The compound of the formula I may be prepared by the following methods:

Method A.

By reacting a compound of the formula

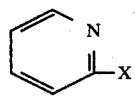

wherein X is halogen, preferably fluorine, chlorine or bromine, with a compound of the formula

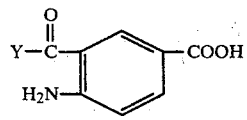

wherein Y is alkoxy,
at elevated temperatures, preferably in the range of about 120° to 160° C. The reaction may be carried out in the absence of a solvent or also in a high-boiling-point solvent, such as dimethylformamide or sulfolane, and advantageously in the presence of an acid acceptor. An excess of the reactant of the formula III may serve as an acid acceptor.

The starting compounds of the formulas II and III are known compounds and can be obtained by conventional methods.

Method B.

By oxidizing a compound of the formula

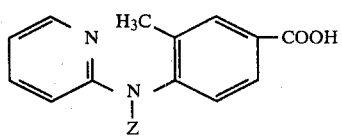

wherein Z is acyl, preferably lower alkanoyl, with a strong oxidizing agent at elevated temperatures, followed by acidification of the reaction mixture. For example, the oxidation can be effected with an aqueous solution of potassium permanganate buffered with magnesium sulfate. Examples of acids which can be used for subsequent acidification are mineral acids such as hydrochloric acid, or also organic acids such as acetic acid.

The starting compounds of the formula IV can be prepared by conventional methods. The carboxyl substituent in formula IV can also be formed in situ from the corresponding methyl-substituted compound or from other correspondingly substituted compounds which are converted into the carboxyl-substituted compound under the reaction conditions.

Method C.

By converting the substituent R in a compound of the formula

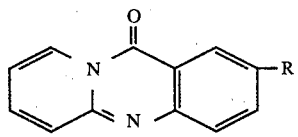

wherein R is a precursor of carboxyl, into carboxyl.

The conversion can be effected by conventional methods. For example, by hydrolysis of a corresponding ester or amide, or also by oxidation of the corresponding methyl-substituted compound with potassium permanganate, for instance.

The starting compounds of the formula V may be prepared either by methods A or B, or by other known methods.

The end product of the formula I obtained by methods A–C forms salts with inorganic or organic bases. These salts may be prepared by conventional methods. Conversely, if a salt of the compound of the formula I is obtained as the end product, the free acid of the formula I may be liberated therefrom by conventional methods.

The following example illustrates the present invention and will enable others skilled in the art to understand it more completely. It should be understood, however, that the invention is not limited solely to the particular example given below.

EXAMPLE 1

11-Oxo-11-H-pyrido[2,1-b]quinazoline-2-carboxylic acid by method B 60 gm of pyridyl(2)-N-(2,4-dimethyl-phenyl)-acetamide were oxidized with 218 gm of potassium permanganate and 75.5 gm of magnesium sulfate in 2 liters of water at a temperature of 40°–90° C. The manganese dioxide which had separated out was suction-filtered off, the filtrate was acidified with acetic acid, and the substance which slowly crystallized out of the acidic solution was collected by suction filtration and then stirred for one hour at 60°–70° C. with a five-fold amount of concentrated hydrochloric acid. Thereafter, the solution was diluted with ten times its volume of water, whereupon the reaction product gradually precipitated out. The precipitate was collected and washed with water and acetonitrile, yielding the compound of the formula

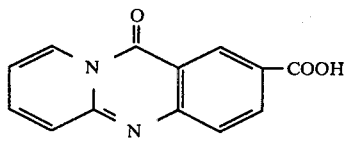

Elemental analysis: $C_{13}H_8H_2O_3$, Calculated: C-65.00%; H-3.33%; H-11.67%, Found: C-64.95%; H-3.46%; H-11.58%.

The starting compound, pyridyl(2)-N-(2,4-dimethylphenyl)-acetamide, was prepared by condensation of equimolar amounts of 2,4-dimethyl-aniline and 2-bromo-pyridine at 160°–180° C. to form 2,4-dimethyl-N-pyridyl(2)-aniline which, after purification via its furmarate, had a melting point of 65°–68° C. and heating the intermediate with acetic acid anhydride.

(a) The sodium salt of 11-oxo-11-H-pyrido[2,1-b]-quinazoline-2-carboxylic acid was obtained by dissolving the acid in water, adding the calculated amount of sodium bicarbonate, and precipitating the salt with ethanol.

(b) The ethanolamine salt was obtained by suspending 1.2 gm of the free acid in 3 ml of water, adding 0.31 ml of ethanolamine thereto, and precipitating the salt with acetonitrile.

Elemental analysis: $C_{15}H_{15}N_3O_4 \cdot H_2O$, Calculated: C-56.43%; H-5.33%; N-13.17%, Found: C-57.25%, H-4.96%, N-13.46%.

(c) The triethanolamine salt, which decomposed above 200° C., was obtained by suspending 2.4 gm of the free acid in 20 ml of acetonitrile, and adding 3.6 gm of about 85% triethanolamine to the suspension.

Elemental analysis: $C_{19}H_{23}N_3O_6$ Calculated: C-58.61%; H-5.91%; N-10.80% Found: C-58.80%; H-5.72%; N-11.00%.

The compounds of this invention, that is, the compound of the formula I above and salts thereof formed with bases, have useful pharmacodynamic properties. More particularly, they exhibit primarily antiallergic activity, but also muscle-relaxing (bronchodilating) and vasodilating activities in warm-blooded animals, such as rats.

The compounds are therefore useful for the prophylaxis and treatment of various allergic disorders, such as asthma, hay fever conjunctivitis, urticaria, eczema, atopic dermatitis and the like. The principal advantage of the compounds of the present invention resides in their long duration of effective action, their peroral efficacy and their favorable absorption quotient.

The antiallergic activity of the compounds of the present invention was ascertained and compared to that of structurally related known compounds by the anaphylactic dextran reaction method, where A = 11-Oxo-11H-pyrido[2,1-b]quinazoline-2-carboxylic acid, described in Example 1 of the present disclosure;

B = 11-Oxo-11H-pyrido[2,1-b]quinazoline-1-carboxylic acid, generically disclosed in U.S. Pat. No. 4,033,961;

C = 11-Oxo-11H-pyrido[2,1-b]quinazoline-4-carboxylic acid, generically disclosed in U.S. Pat. No. 4,033,961;

D = 11-Oxo-11H-pyrido[2,1-b]quinazoline-7-carboxylic acid, generically disclosed in U.S. Pat. No. 4,033,961; and E = 11-Oxo-11H-pyrido[2,1-b]-quinazoline-8-carboxylic acid, disclosed in Example 1 of U.S. Pat. No. 4,033,961.

Principle:

Dextran induces in the rat a de-granulation of mast cells and thus the release of mediator substances such as histamine and serotonin, with consequent edema formation. The reaction manifests itself in a manner similar to anaphylaxis [see Morrison et al., J.exp.Med. 103, 399 (1956)].

Method

Fasted male laboratory rats (Chbb:Thom.SPF) having a body weight of 120–180 gm were used as the test animals; they were initially kept in wire cages, and after provocation of the reaction on chaff. The allergic reaction was released by subplantar injection into the right hind paw of 100 μgm of dextran (mol. wt. 60,000) in 0.1 ml of physiological sodium chloride solution. The degree of inflammatory swelling was determined by dorso-plantar measurement of the thickness of the paw [see Doepfner et al., Int. Arch. Allergy 12, 89 (1958)] in 1/100 mm; swelling was defined as the difference between the paw thickness 30 minutes after the dextran injection and the paw thickness before the dextran injection. For the dextran injection and the paw thickness measurements the animal was placed under light general anesthesia with ether (etherrausch).

The test compound was administered shortly before release of the allergic reaction in sodium chloride solution i.v. (0.5 ml/100 gm body weight), or 10 minutes before in 1% tylose 2000 p.o. (1 ml/100 gm body weight). Control animals received only the vehicle.

From the raw data thus obtained the percentage of swelling inhibition was calculated from the average paw swelling in the treated animals (T) and in the control animals (K) in accordance with the formula $$\% \text{ swelling inhibition} = 100 \times \frac{1-T}{K}.$$

By graphic extrapolation the dose of test compound was determined which produced a 35% reduction of the swelling ($ED_{35}$). For graphic representation of percentage inhibition values the standard error ($s_{\bar{x}}$—) was determined according to Fenner, Naturwissenschaften 19, 310 (1931).

Results:

Dextran edema test

For the anaphylactoid dextran reaction in the rat paw the following values were obtained at a dose of 100 mgm/kg:

| Compound | % Inhibition of swelling |
|---|---|
| B | 0 |
| C | 10 |
| D | 38 |

These values show that the $ED_{35}$ for compounds B and C is greater than 100 mgm/kg p.o., and that for compound D the $ED_{35}$ is close to 100 mgm/kg p.o. In contrast thereto, the $ED_{35}$ for compound A was found to be 4.0 mgm/kg p.o. by this test, and for compound E it was found to be 4.4 mgm/kg p.o. The $ED_{35}$ for compound A was found to be 2.1 mgm/kg i.v., and for compound E it was found to be 1.1 mgm/kg i.v.

Absorption

For the efficacy of a pharmaceutical which is to be administered perorally, the absorption is of particular advantage. Conclusions regarding the absorption can be drawn from a comparison of the $ED_{35}$—values p.o. and i.v.; the smaller the quotient $ED_{35}$ p.o./$ED_{35}$i.v., the better the absorption.

| Compound | $ED_{35}$ mgm/kg | | Quotient |
| --- | --- | --- | --- |
| | p.o. | i.v. | $ED_{35}$p.o./$ED_{35}$i.v. |
| A | 4.0 | 2.1 | 1.9 |
| E | 4.4 | 1.1 | 4.0 |

The extraordinarily favorable absorption quotient of the compound of the present invention is clearly superior to that of the prior art compound having $ED_{35}$-values of comparable magnitude, which represents a significant therapeutic advantage.

For pharmaceutical purposes the compounds of the present invention are administered to warm-blooded animals perorally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, and the like. The effective dosage range for oral administration is about 1 to 50 mgm/kg body weight.

The following example illustrates a pharmaceutical dosage unit composition comprising a compound of the present invention as an active ingredient and represents the best mode contemplated of carrying out the invention. The parts are parts by weight.

EXAMPLE 2

| Tablets | |
| --- | --- |
| The tablet composition is compounded from the following ingredients: | |
| 11-Oxo-11-H-pyrido[2,1-b]-quinazoline-2-carboxylic acid | 0.100 parts |
| Stearic acid | 0.010 parts |
| Glucose | 1.890 parts |
| Total | 2.000 parts |

Preparation:

The ingredients are admixed and processed in conventional manner, and the composition is compressed into 2 gm-tablets, each of which contains 0.1 gm of the active ingredient.

Any one of the other compounds of this invention may be substituted for the particular active ingredient in illustrative Example 2. Likewise, the amount of active ingredient in this example may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 11-Oxo-11H-pyrido[2,1-b]quinazoline-2-carboxylic acid or a non-toxic, pharmacologically acceptable salt thereof.

2. An antiallergic pharmaceutical composition consisting essentially of an inert pharmaceutical carrier and an effective antiallergic amount of a compound of claim 1.

3. The method of suppressing allergic reactions in warm-blooded animals, which comprises perorally administering to said animal an effective antiallergic amount of a compound of claim 1.

* * * * *

UNITED STATES PATENT AND TRADEMARK OFFICE
CERTIFICATE OF CORRECTION

PATENT NO. : 4,332,802

DATED : June 1, 1982

INVENTOR(S) : KURT SCHROMM ET AL.

It is certified that error appears in the above-identified patent and that said Letters Patent is hereby corrected as shown below:

Title page [75]: "Anton Mentrüp" should read

-- Anton Mentrup --.

Column 3, line 23: "furmarate" should read -- fumarate

Signed and Sealed this

Twenty-fourth Day of January 1984

[SEAL]

Attest:

GERALD J. MOSSINGHOFF

Attesting Officer

Commissioner of Patents and Trademarks